United States Patent [19]
Strayer

[11] Patent Number: 5,863,794
[45] Date of Patent: Jan. 26, 1999

[54] SV40 VIRAL VECTORS FOR TARGETED INTEGRATION INTO CELLS

[75] Inventor: David Strayer, Newtown Square, Pa.

[73] Assignee: Thomas Jefferson University, Philadelphia, Pa.

[21] Appl. No.: 1,925

[22] Filed: Dec. 31, 1997

Related U.S. Application Data

[60] Provisional application No. 60/034,023 Jan. 8, 1997.
[51] Int. Cl.[6] ................................................ C12N 15/86
[52] U.S. Cl. ........................................................... 435/320.1
[58] Field of Search ................................ 435/320.1, 235.1

[56] References Cited

PUBLICATIONS

Ochman et al., "Genetic Applications of an Inverse Polymerase Chain Reaction", *Genetics* 1988 120:621–623.
Takagi et al., "A Rapid and Efficient Protocol of the Inverted PCR Using Two Primer Pairs", *Biotechniques* 1992 13:176–178.
Strayer et al., *Gene Therapy*, vol. 3, 1996, pp. 581–587 (Abstract only).

*Primary Examiner*—James Ketter
*Attorney, Agent, or Firm*—Law Offices of Jane Massey Licata

[57] ABSTRACT

A vector capable of integrating into a selected site of a cell's genome is provided which contains a replication-deficient SV40 virus and a nucleic acid sequence flanked with integration promotion sequences.

2 Claims, 1 Drawing Sheet

SV40 VIRAL VECTORS FOR TARGETED INTEGRATION INTO CELLS

This application claims the benefits of U.S. Provisional Application No. 60/034,023, filed Jan. 8, 1997.

INTRODUCTION

This invention was made in the course of research sponsored by the National Institutes of Health. The U.S. Government may have certain rights in this invention.

FIELD OF THE INVENTION

The present invention relates to the incorporation of integration promotion sequences into an SV40 viral vector to direct integration of the vector into a selected site of a cell's genome. This ability to direct integration of the vector to a selected site of the genome of a cell makes the vectors especially useful, for example, in replacing mutated portions of a genome with a non-mutated nucleic acid sequence; interrupting expression of a harmful or overexpressed protein by insertion of a noncoding nucleic acid sequence into the portion of the genome which expresses the harmful or overexpressed protein; and in directing integration of a selected gene to a portion of the genome which is constitutively expressed.

BACKGROUND OF THE INVENTION

Gene transduction, the introduction of foreign genetic materials into cells or organisms, is a requisite technology involved in approaches to correcting genetic abnormalities, i.e., gene therapy. Genes can be transfected into cells by physical means such as scrape loading or ballistic penetration; by chemical means such as co-precipitation of DNA with calcium phosphate or liposomal encapsulation; or by electrophysiological means such as electroporation. However, these methods are relatively inefficient and the cells are significantly perturbed from their normal environment. In contrast, transduction of genes by means of recombinant viruses into a cell that is held in a physiologic environment takes advantage of the relative efficiency of viral infection processes.

Current gene therapy involves infection of organisms or cells with replication-deficient recombinant viruses containing the desired gene or genes. These viruses introduce the desired gene or genes into target cells by relatively efficient infection processes. However, these viruses are rendered deficient in some later replication step so that the primary infection does not produce progeny virus thereby circumventing the problem of propagating a deleterious full lytic viral infection cycle. Ideally, this virus only infects target cells, functionally expresses the gene it carries, and perpetuates the expression of this gene in the target cell and its progeny. Practically, however, this objective has been difficult to achieve. The reasons for these difficulties lie in the nature of the viral agents used to introduce the foreign gene(s) in question.

There are a number of replication-deficient viruses which are currently being used or have been proposed as gene transduction vectors. Examples include retroviruses, adenoviruses, adeno-associated viruses and herpesviruses. Although it has been demonstrated that gene therapy is possible using such viruses, all involve significant problems that limit or preclude their applicability to gene therapy in a clinically relevant setting.

Retroviruses such as MuLv may integrate into host cellular genomes, but these viral vectors only infect dividing cells. Thus, while they may be highly effective as transduction vectors, they cannot be used to stimulate gene expression in resting cells. This is a significant limitation for their utility in the treatment of many genetic disorders. Another limitation is that retroviruses become inactive at high concentrations and on exposure to human blood. Therefore, retroviruses cannot be concentrated in high enough amounts to avoid administering enormous volumes of fluid containing the recombinant viruses.

Adenovirus DNA does not integrate into the host genome, so when an infected cell divides, the viral DNA which is not replicated is then present in one-half of daughter cells. A second division dilutes still further the transduced gene until it is eventually lost to the cell progeny. Therefore, adenovirus mediated gene transduction allows expression in resting cells but does not permit transmission of gene expression to daughter cells. A further significant limitation is that adenovirus elicits a destructive immune response on the part of the host immune system that leads to the elimination of the desired transduced cells, much as the body would clear a clinical virus infection (e.g., influenza, rhinovirus).

Adeno-associated virus (AAV), but probably not recombinant AAV, integrates into the host genome. The wild-type AAV has a preference for an integration site that is at or near an important gene translocation site for some acute leukemias. Furthermore, like retroviruses, adeno-associated virus can not be produced at high virus concentrations.

Herpesviruses have only recently been proposed as vectors for gene transduction and their use has not been fully evaluated at this time. However, they appear to be most effective in the central nervous system and are not clearly useful in other organ targets.

SV40 (Simian Virus-40) has been demonstrated to provide a unique vector for gene therapy which has several advantages over any of the currently available viral vectors. It has now been found that integration of this vector into a selected site of the genome of a cell can be directed by flanking a nucleic acid sequence to be integrated with integration promotion sequences designed to target integration of the vector to the selected site of the cell's genome.

SUMMARY OF THE INVENTION

An object of the present invention is to provide a vector comprising a replication-deficient SV40 virus and a nucleic acid sequence flanked at either end with integration promotion sequences designed to target integration of the vector into a selected site of the genome of a cell.

DETAILED DESCRIPTION OF INVENTION

Figure 1:
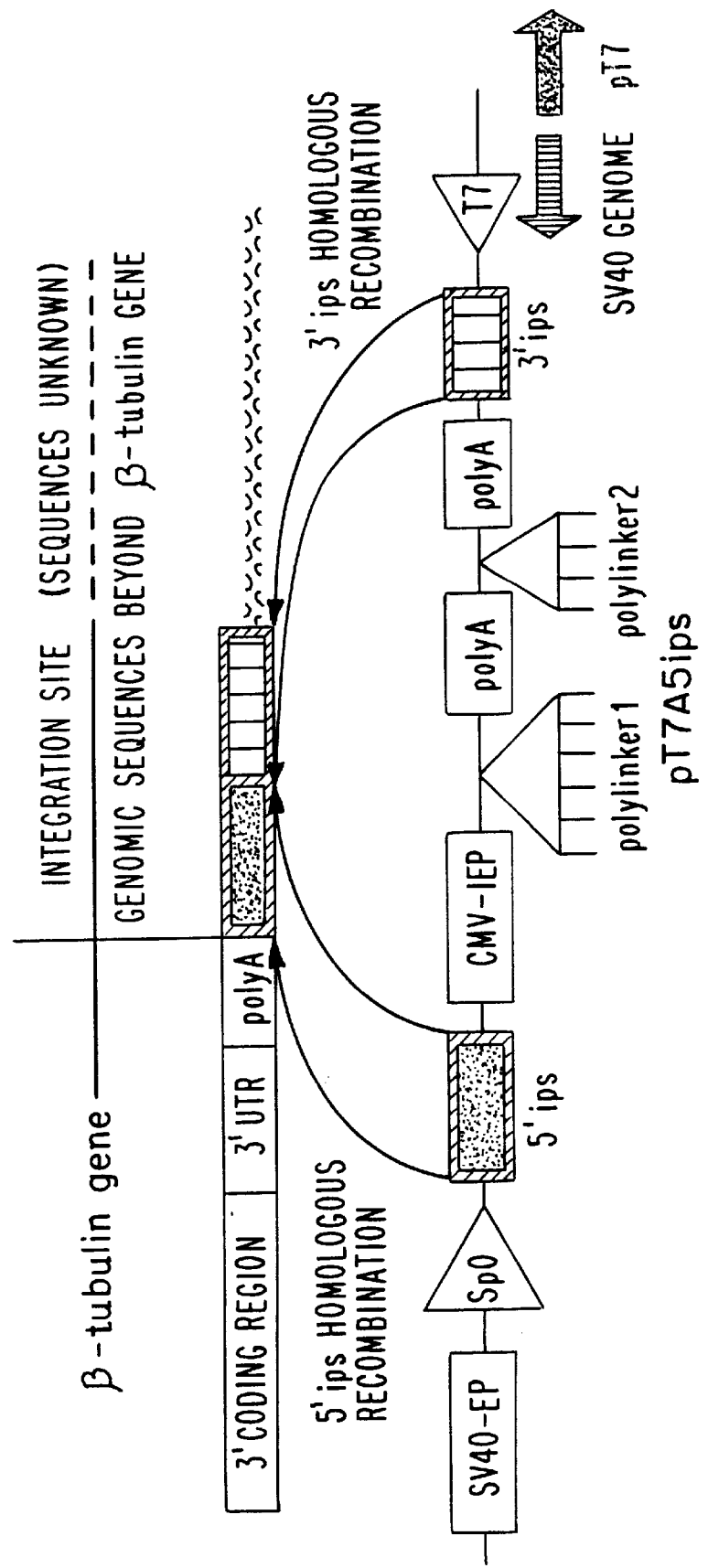
FIG. 1 provides a schematic of one embodiment of the present invention of a replication-deficient SV40 viral vector having flanking sequences complementary to the targeted genomic β-tubulin gene.

A vector, the integration of which can be directed to any selected site in a cell's genome, has now been developed. This vector comprises a SV40 replication-deficient virus and a nucleic acid sequence flanked by integration promotion sequences designed to target integration of the vector into a selected site of the genome of a cell.

By "integration promotion sequences" it is meant a DNA sequence of a length and complementarity which permits the sequence to hybridize specifically to a selected site in a cell's genome, thus facilitating integration of a nucleic acid sequence flanked by the integration promotion sequences of the SV40 viral vector into the selected site of the genome. Selection of integration promotion sequences can be routinely performed by those of skill in the art based upon the purpose for which the vector and nucleic acid sequence in the vector are being used.

For example, in one embodiment, wherein expression of the nucleic acid sequence of the vector is desired, the selected site targeted for integration is one which is: (i) constitutively expressed, i.e., in open chromatin; (ii) beyond (i.e., 3' to) the target gene's poly A signal, to avoid disruption of that gene's transcript; and (iii) characterized structurally for enough of the human gene to make targeting feasible. Examples of such areas in the cell's genome are well known to those skilled in the art and are commonly referred to as "housekeeping genes". Examples include, but are not limited to, cytoskeletal genes, cytochrome genes and mitochondrial genes. Accordingly, in this embodiment, the integration promotion sequences flanking the nucleic acid sequence of the vector comprise DNA sequences complementary to a portion of one of these constitutively expressed genes which will not disrupt the gene's transcript and the nucleic acid sequence will be a selected gene to be encoded by the cell. Nucleic acid sequences of this embodiment may also encode antisense oligonucleotides or ribozymes.

In another embodiment, the site targeted for integration is selected because of its proximity to a mutated gene. In this embodiment, the integration promotion sequences comprise DNA sequences complementary to a portion of the genome next to the mutation which are capable of hybridizing specifically to that portion of the cell's genome. The nucleic acid sequence flanked by the integration promotion sequences of this embodiment of the vector comprises a replacement for the mutated gene. Accordingly, if the mutation results from only a single mutated base-pair in the cell's genome, the nucleic acid sequence of the vector may comprise only a single base to replace the mutated portion. Alternatively, the nucleic acid sequence may comprise multiple bases to replace a larger portion of the genome.

In yet another embodiment, the site targeted for integration is a gene which is overexpressed or which expresses a harmful protein. In this embodiment, the integration promotion sequence comprises DNA complementary to a portion of the harmful or overexpressed gene and the nucleic acid sequence will be a sequence which inhibits expression of this protein upon integration into the genome. For example, in this embodiment, the nucleic acid sequence can be a nonsense sequence which disrupts expression of the gene.

SV40 is a relatively small (5.3 kilobases (kb)) double-stranded DNA virus that normally infects monkeys, but also infects other mammals. SV40 is very safe. Millions of people received wild type SV40 in early batches of polio vaccines, without documented adverse consequences. Further, this virus can be concentrated to high titers for treatment of large cell pools. In addition, it can be used in vivo in humans. SV40 also infects and expresses its genes in many cell types and in animals that are relevant models for HIV infection. It can be made replication-deficient, and relatively nonimmunogenic. In addition, SV40 is easily handled and packaged without helper virus to allow generation of many variant constructs to optimize expression and delivery. SV40 expresses genes stably either in integrated form or episomally.

SV40-derived vectors are effective gene transfer agents in vitro and in vivo; in particular, they are effective via direct IV inoculation in vivo. In addition, long term transgene expression and genomic integration are observed in vivo without evidence of immunologically mediated elimination of expressing cells. SV40 also infects and expresses transgenes in resting, unselected phytohemagglutinin (PHA)—stimulated blood mononuclear cells (PBMC). Further, with SV40-based vectors very high levels of foreign gene expression are achieved in human T cells. In addition, active ribozyme. introduced through an SV40 viral vector, reduced target mRNA by approximately 90% in human cells.

SV40-mediated gene transfer was demonstrated in vitro in human, monkey and mouse cells from different tissues, and in vivo in BALB/c mice. Luciferase (luc) was used as a reporter gene to yield SVluc. SVluc was inoculated directly into mice, and used to treat bone marrow cells ex vivo that were then reinfused in vivo. Luc protein was detected in multiple organs from 3 to 376 days (the final assay time), and, in the bone marrow transfer experiments, in 20–25% of peripheral blood nucleated cells for the same duration without evidence of inflammatory reaction to any of the transduced cells. Thus, SV40 transfers sustained transgene expression to bone marrow-derived cells and other tissues for more than one year. Additional studies demonstrate the ability of SV40 to transduce human PBMC and other cells, and to express an array of transgenes effectively including the HIV antibody, anti-IN SFv, and catalytic ribozyme. Transgene expression in unselected SV40-transduced cells exceeded, often by greater than 10-fold, levels attained in selected MuLV-transduced cells. In addition, SV40 has been shown to effectively transduce ribozyme activity against an endogenous cellular transcript, as measured in unselected human cells, and using either pol II or pol III promoters.

Replication-deficient SV40 constructs are prepared in a carrier plasmid such as pBR322, pGEM13 or pT7 by excising the large T antigen (Tag), which is required for virus replication, and replacing it with a polylinker, just 3' to the early promoter. Tag is supplied in trans by packaging cells, to allow production of replication-incompetent virus. Removing the Tag gene creates greater than 2.4 kb of space for inserted DNA. It also renders resulting viruses replication-incompetent, eliminates an important viral antigen and prevents transcription of viral capsid proteins. In a preferred embodiment, high copy number plasmids pT7 and pGEM13 are used to carry the viral genome. With these carrier plasmids, rare restriction sites, such as Pme I for pT7 and Not I for pGEM13, can be used to clone the SV40 genome into these plasmids. Additional restriction sites can be added to the polylinker.

It has now been found that integration of the vector into the genome of a selected cell can be directed by flanking a nucleic acid sequence to be integrated into the genome of a cell with integration promotion sequences designed to target a selected site in the genome of the cell. The ability of a replication-deficient SV40 vector comprising a nucleic acid sequence flanked with integration promotion sequences to target a selected site in the genome of the cell was demonstrated. In these experiments, an SV40 derivative construct was prepared wherein an antibody gene against HIV driven by the CMV intermediate-early promoter was flanked by 50 bp upstream and 50 bp downstream of the β-tubulin gene was prepared. See FIG. 1. More specifically, a DNA sequence from the 3' end of the published human β-tubulin gene consisting of (5'-AGGAAGAGAGGTCACCCCTA-CCCTCCCTCCCCGCTTGCCTGCCTCACCCTCAATA-AATAAATTAA-3', SEQ ID NO: 1) was placed in front of a CMV promoter, followed by cDNA encoding a single chain Fv antibody to HIV integrase referred to as SV-Aw, the SV40 poly A sequence, and a second DNA sequence from the human β-tubulin gene consisting of (5'-TGTTGTC-ATGGATGTTCTGCCGAATCCCTCTTTCCTCTCTTAC-AGCAA-3', SEQ ID NO: 2). Using this vector, integration of Aw, driven by CMV promoter, was directed to a portion of the genome that is transcriptionally active in all cells but does not interfere with the transcription of expression of a necessary gene. This vector is referred to herein SV-AW.ips. In this particular embodiment, the integration promotion sequences consist of DNA complementary to a portion of the β-tubulin gene. However, as will be obvious to those of skill in the art upon this disclosure, in this embodiment of the present invention, wherein the vector is used to integrate a selected gene to be expressed by the cell into the cell's genome, the integration promotion sequences can be complementary to any constitutively expressed portion of the genome which does not disrupt the gene's transcript.

Integration was detected by inverted PCR in accordance with procedures described by Ochman et al. *Genetics* 1988 120: 621–623 and Takagi et al. *Biotechniques* 1992 13: 176–178. Following PCR, the virus sequences of the amplified DNA fragment were used in Southern hybridization to probe the electrophoresed DNA fragments. Free virus genome has a PCR product of 320 bp. This product was observed when SupT1 cells infected with SV-AW.ips were harvested immediately after addition of the virus and when DNA was made from the virus stock, without infecting SupT1 cells. By 4 days after infection, however, a distinct band at approximately the predicted position corresponding to the size of the integrated DNA in SupT1 cells infected with SV-AW.ips was observed thus demonstrating targeted integration.

The replication-deficient SV40 vectors of the present invention are useful in gene therapy. The term "gene therapy" includes not only the processes of gene knockout and gene targeting, but also gene repair. By "gene repair" it is meant to include directing integration of a transferred fragment of DNA to a specific site in the cellular genome and allowing it to recombine at that point with an abnormal or mutated gene, or an undesirable or overexpressed gene. For example, a mutation in the ras oncogene or p53 gene could be repaired. Alternatively, a fragment of the genome, the expression of which is not desired can be interrupted by insertion of a nucleic acid sequence, such as a nonsense sequence, at that site of the genome. This may useful, for example, in trying to prevent expression of integrated human papillomavirus sequences in cervical epithelium. Other diseases wherein prevention of expression of a protein is desirable and the vector of the present invention is useful are well known to those skilled in the art.

This novel vector system can also be used to deliver intracellular antibodies against HIV and SIV proteins ex vivo to cultured cells, for reimplantation into animals, and also directly in vivo. It is believed that SV40-mediated transduction of intracellular anti-IN SFv is protective against HIV and SIV infection in vitro and in vivo. SFv can be delivered by SV40 to determine inhibition of IN and other HIV-1 proteins and the effect of this inhibition on progression of HIV infection, in cultured cells and animal models. Data from these experiments can then be used to guide modification of delivery and expression constructs, in order to maximize inhibition of HIV.

Alternatively, the aim of gene therapy can be to introduce a gene from another species into an animal or cells. With the vector of the present invention, it is possible to, for example, introduce a herpesvirus gene such as thymidine kinase (TK) into target cells to render the cells sensitive to certain drugs. In this embodiment, the drug could be a DNA based analog which is metabolized by the thymidine kinase to a toxic metabolite whose purpose is to kill cells bearing the TK gene. New drugs with high specificity for cells bearing this gene, such as tumor cells, can be easily identified with such a test system. In addition, the transduction system can be used to introduce a foreign gene capable of expressing a desired protein into a cell for production of that protein. The expressed protein can then be isolated and purified for a variety of uses well known to those of skill in the art.

The vector can also be used to supplement a deficient or mutant gene by the addition of a normal gene thereby correcting a defect caused by the deficient or mutant gene. For example, using the vector of the present invention, red blood cell precursor cells that contain the sickle hemoglobin gene, which is mutant in the DNA encoding a particular amino acid, can be transduced to express the normal hemoglobin A gene, rectifying the effect of the sickle hemoglobin gene. Alternatively, overexpression of a particular oncogene resulting in exhibition of a cancerous phenotype in a cell can be inhibited by insertion and incorporation of a new sequence into the genome using the vector of the present invention thus reducing or eliminating expression of the oncogene.

The vector of the present invention can also be used to supplement insufficient expression of a structurally normal gene. For example, the pancreatic islet cells from insulin deficient diabetic patients could be transduced with a normal insulin gene having a normal insulin promoter. While individuals suffering from this disease sometimes bear a structurally normal insulin gene, it is not expressed normally. The addition of another copy of the normal gene with its normal promoter could be used to treat the diabetes in these patients.

These vectors are also useful in blocking the expression of a particular gene, the expressed protein of which is either abnormal or undesirable. An example of such a disease is α-1 antitrypsin disease. In this instance, a nucleic acid sequence could either be antisense to the transcript for the undesired gene or could be a catalytic RNA or ribozyme designed to destroy the mRNA for the particular gene. In this embodiment, the target mRNA may be either a normal cellular protein expressed aberrantly, a mutant cellular protein, or even a normal protein, the production of which interferes with a desired effect, for example, an enzyme that metabolizes a drug and prevents it from attaining or maintaining adequate levels.

Presently, linear or circular DNA vectors are introduced into cells by a variety of techniques and are transported to the nucleus where the gene target resides. The vector and target undergo recombination events so that the cellular gene is modified or rendered inoperative. The efficiency with which these DNA vectors work, however, is very low.

The vector of the present invention, however, has a relatively high infectivity to virus particle ratio and can integrate very efficiently into a selected site of the host genome which is transcriptionally active in all cells but which does not interfere with the transcription of expression of a necessary gene. This system carries its own strong promoter sequences. Accordingly, in one embodiment, this vector provides an efficient means for the introduction of selected genes into a cell or animal. For the purposes of this invention, "selected gene" is meant to include, but is not limited to, a gene from a species different to the cell or animal in which it is transduced, a normal gene used to replace a deficient or mutant gene in the same cell or animal in which it is transduced, a normal gene used to supplement insufficient expression of structurally normal gene in the same cell or animal in which it is transduced, or a gene or cDNA which interferes with expression of a gene in a cell or animal. Such genes can be routinely selected by those of skill in the art upon this disclosure. Genes ranging in size from approximately 0.4 kb to approximately 2.2 kb have been transduced into cells using the present invention. However, genes which are less than 0.4 kb and as large as approximately 4.4 kb can also be used. By "animal" it is meant to include, but is not limited to, mammals, fish, amphibians, reptiles, marsupials, and most preferably, humans.

The vector of the present invention can be administered to animals by a number of different routes routinely determined by those of skill in the art based upon the selected foreign gene and target site. For example, in the case of HIV or supplementing a sickle hemoglobin gene with a normal gene in red blood cell precursor cells the target site can be the bone marrow. Thus, the mode of administration could be via autologous bone marrow transplantation wherein bone marrow cells from a patient are transduced with the vector of the present invention and then infused back into the bone marrow of the patient. Other modes of administration which may be appropriate for the vector of the present invention include, but are not limited to, inhalation, intravenous, intracavitary to the bone marrow, subcutaneous, intramuscular, intrathecal, intraperitoneal, or transurethral administration, intranasal or intratracheal installation, or local or topical administration to a mucosal surface either orally, nasally or via suppository. Drug formulations, dosing regimens and administration protocols used with the present invention can be determined easily by one of skill based upon general principles of drug chemistry and testing.

What is claimed is:

1. A vector comprising a replication-deficient SV40 virus and a nucleic acid sequence flanked with selected integration promotion sequences.

2. The gene transduction vector of claim 1 wherein the nucleic acid sequence encodes a selected gene and the integration promotion sequences comprise DNA of the human β-tubulin gene.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 65
        ( B ) TYPE: Nucleic Acid
        ( C ) STRANDEDNESS: Single
        ( D ) TOPOLOGY: Linear ( i v ) ANTI-SENSE: NO ( x i ) SEQUENCE DESCRIPTION: SEQ ID NO: 1:

AGGAAGAGAG GTCACCCCTA CCCTCCCTCC CCGCTTGCCT GCCTCACCCT                    50

CAATAAATAA ATTAA                                                         65

( 2 ) INFORMATION FOR SEQ ID NO: 2:

( i ) SEQUENCE CHARACTERISTICS:
        ( A ) LENGTH: 48
        ( B ) TYPE: Nucleic Acid
        ( C ) STRANDEDNESS: Single
        ( D ) TOPOLOGY: Linear ( i v ) ANTI-SENSE: NO ( x i ) SEQUENCE DESCRIPTION: SEQ ID NO: 2:

TGTTGTCATG GATGTTCTGC CGAATCCCTC TTTCCTCTCT TACAGCAA                      48